(12) United States Patent
Liu et al.

(10) Patent No.: US 8,557,976 B2
(45) Date of Patent: Oct. 15, 2013

(54) MICROBIAL CONSORTIA AND METHODS FOR THEIR USE

(75) Inventors: Chi-Li Liu, Decatur, IL (US); Travis Aaron Mahan, Decatur, IL (US); Edward Farley, Macon, IL (US)

(73) Assignee: Tate & Lyle Technology Limited, London (GB)

( * ) Notice: Subject to any disclaimer, the term of this patent is extended or adjusted under 35 U.S.C. 154(b) by 588 days.

(21) Appl. No.: 12/366,115

(22) Filed: Feb. 5, 2009

(65) Prior Publication Data

US 2009/0234113 A1  Sep. 17, 2009

Related U.S. Application Data

(60) Provisional application No. 61/069,303, filed on Mar. 13, 2008.

(51) Int. Cl.
*C13K 13/00* (2006.01)

(52) U.S. Cl.
USPC ............... 536/123.13; 435/252.1; 435/253.6; 435/262.5

(58) Field of Classification Search
None
See application file for complete search history.

(56) References Cited

U.S. PATENT DOCUMENTS

| 4,950,746 A | 8/1990 | Navia |
|---|---|---|
| 4,980,463 A | 12/1990 | Walkup et al. |
| 5,023,659 A | 6/1991 | Beasely |
| 5,034,551 A | 7/1991 | Vernon et al. |
| 5,089,608 A | 2/1992 | Walkup et al. |
| 5,470,969 A | 11/1995 | Sankey et al. |
| 5,498,709 A | 3/1996 | Navia et al. |
| 6,890,581 B2 | 5/2005 | Vernon et al. |

FOREIGN PATENT DOCUMENTS

WO   WO 2006/130169   12/2006

OTHER PUBLICATIONS

Duhamel et al., Water Research, 2002, vol. 36, p. 4193-4202.*
Kataky et al., Analyst, 2001, vol. 126, p. 1901-1906.*
Combined Search and Examination Report dated Sep. 1, 2008, for GB Application No. 0807978,2, 6 pgs.
Cussac, Yolaine, International Preliminary Report on Patentability dated Sep. 14, 2010, for PCT Application No. US2009/033531, 6 pgs.
Labare, M. P., et al.; "Microbial cometabolism of sucralose, a chlorinated disaccharide, in environmental samples", Journal—Appl Microbial Biotechnol (1994) 42:173-178, Great Britain.
Roscoe, Richard, et al.; "International Search Report"; report; Jul. 24, 2009; 12 pp; European Patent Office, Rijswijk, The Netherlands.
Labare, Michael P., et al.; "Biodegradation of Sucralose, a Chlorinated Carbohydrate, in Samples of Natural Environments"; Environmental Toxicology and Chemistry; 1993, pp. 797-804, vol. 12, No. 5, New York, USA.

* cited by examiner

*Primary Examiner* — Kade Ariani
(74) *Attorney, Agent, or Firm* — RatnerPrestia

(57) ABSTRACT

Isolated microbial consortia capable of degrading chlorinated carbohydrates and a method to acclimatize microbes to degrade chlorinated carbohydrates under specific conditions of temperature and salt are described. Also described is a method for using microbial consortia to degrade chlorinated carbohydrates in a waste stream.

24 Claims, 3 Drawing Sheets

MICROBIAL CONSORTIA AND METHODS FOR THEIR USE

BACKGROUND OF THE INVENTION

Sucralose (4,1',6'-trichloro-4,1',6'-trideoxygalactosucrose), a high-intensity sweetener made from sucrose, can be used in many food and beverage applications.

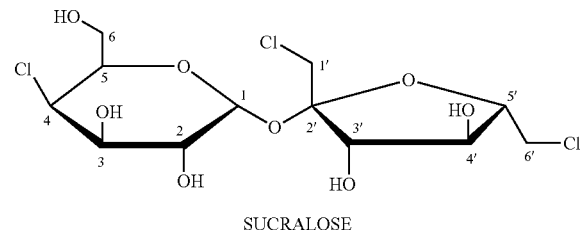

SUCRALOSE

A number of different synthetic routes for the preparation of sucralose have been developed in which the reactive hydroxyl in the 6 position is first blocked with an acyl group to form a sucrose-6-acylate. The sucrose-6-acylate is then chlorinated to replace the hydroxyls at the 4,1' and 6' positions to produce 4,1',6'-trichloro-4,1',6'-trideoxygalactosucrose-6-acylate (sucralose-6-acylate), followed by hydrolysis to remove the acyl substituent and thereby produce sucralose. Several synthesis routes for formation of the sucrose-6-acylates involve tin-mediated acylation reactions, with illustrative examples being disclosed in U.S. Pat. Nos. 4,950,746; 5,023,329; 5,089,608; 5,034,551; and 5,470,969, all of which are incorporated herein by reference.

Various chlorinating agents may be used to chlorinate the sucrose-6-acylate, and most commonly a Vilsmeler-type salt, such as Arnold's Reagent, will be used. One suitable chlorination process is disclosed by Walkup et al. (U.S. Pat. No. 4,980,463), in which a tertiary amide, typically N,N-dimethylformamide ("DMF"), is used as the chlorination reaction solvent. After the chlorination is complete, the reaction mixture is neutralized with aqueous alkali to regenerate the hydroxyl groups at positions 2,3,3', and 4' of the sucralose-6-acylate, which yields the sucralose-6-acylate in an aqueous solution, accompanied by the tertiary amide solvent and salts resulting from reactions of the chlorination reagent. The sucralose-6-acylate is then deacylated to produce sucralose. One suitable process is taught by Navia et al., U.S. Pat. No. 5,498,709, the entire disclosure of which is incorporated herein by reference.

Various chlorinated carbohydrate compounds are typically formed during the synthesis of sucralose. These compounds can be de-chlorinated chemically to provide waste products that are readily biodegraded. However, chemical de-chlorination typically requires high temperatures and the use of caustic solutions, which can negatively affect subsequent biodegradation of the waste products. A more cost-effective and environmentally friendly method to degrade chlorinated carbohydrates is desired.

SUMMARY OF THE INVENTION

The invention provides an isolated microbial consortium that is capable of degrading chlorinated carbohydrates, wherein the isolated microbial consortium grows or survives in a medium comprising chlorinated carbohydrates and wherein the microbial consortium degrades chlorinated carbohydrates.

The invention further provides an isolated microbial consortium, wherein the microbial consortium is capable of degrading chlorinated carbohydrates in a waste stream generated in the production of sucralose.

Also provided is a method for degrading chlorinated carbohydrates, the method comprising the steps of a) inoculating a medium containing chlorinated carbohydrates with an isolated microbial consortium capable of degrading the chlorinated carbohydrates; and b) incubating the microbial consortium in the medium.

Further provided is a method for developing a microbial consortium capable of degrading chlorinated carbohydrates, comprising the steps of a) providing an environmental sample containing microbes; b) incubating microbes in the sample in a defined medium comprising one or more organic solvents wherein the temperature of incubation is from about 15° C. to about 55° C. and the chloride salt concentration of the medium is about 4.5 percent or less; c) selecting a microbial consortium present in the medium after step b) that degrades one or more of the organic solvents; d) subsequently replacing the medium of the selected consortium with a medium comprising the chlorinated carbohydrates, and e) selecting a consortium that degrades chlorinated carbohydrates by monitoring the medium for degradation of the chlorinated carbohydrates.

Additionally provided is a method of producing sucralose comprising the steps of a) maintaining a solution comprising a sucralose-6-acylate in an aqueous solvent under conditions sufficient to deacylate substantially all of the sucralose-6-acylate; b) subsequently recovering the sucralose; and c) degrading chlorinated carbohydrates present after the deacylation by a method comprising the steps of i) inoculating a solution comprising the chlorinated carbohydrates with an isolated microbial consortium that degrades the chlorinated carbohydrates; and ii) incubating the microbial consortium in the solution.

A. Biodegradation of total chlorinated carbohydrates in waste stream 1 by consortia P-3 and P-4.

B. Biodegradation of total chlorinated carbohydrates in waste stream 2 by consortia P-5, P-6, and P-7.

Figure 3:
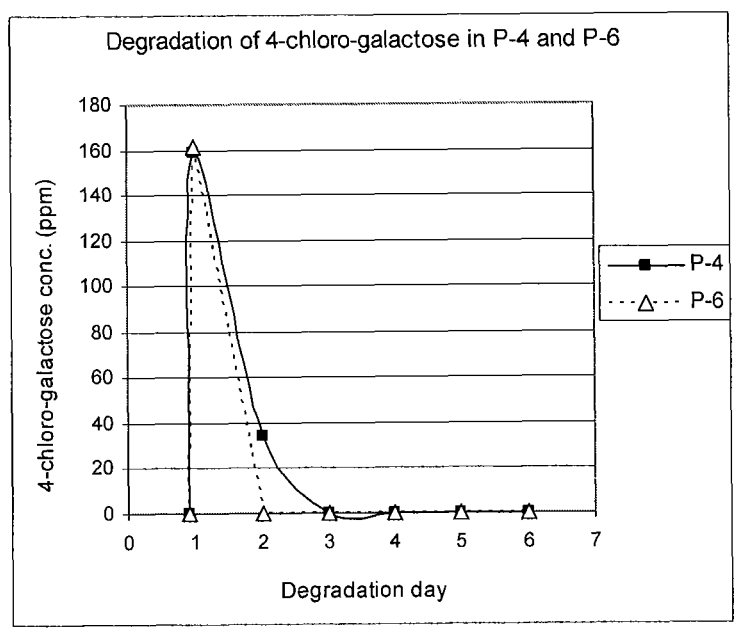

FIG. 3. Biodegradation of 4-chloro-galactose in synthetic medium by consortia P-4 and P-6.

DETAILED DESCRIPTION OF THE INVENTION

A method is described for acclimatizing microorganisms to degrade chlorinated carbohydrates that may be found in waste streams. This method has been utilized to produce microbial consortia that can be used to degrade chlorinated carbohydrates. These consortia were deposited with the National Center for Agricultural Utilization Research, Northern Regional Research Laboratories, Peoria, Ill. on Jan. 11, 2008, by Dr. Chi-Li Liu for Tate & Lyle as accession numbers NRRL B-50091, NRRL B-50092, NRRL B-50093, NRRL B-50094, NRRL B-50095, NRRL B-50096, NRRL B-50097, and NRRL B-50098, and are described in Example 3. These microbial consortia contain groups of microbial species adapted to co-exist in an environment in which certain parameters, such as food component(s), temperature, salt concentration, or combinations of these parameters provide selective pressure for survival and biodegradation. By employing microbial consortia for biodegradation, the need to chemically de-chlorinate chlorinated carbohydrates may be reduced or even completely avoided.

In this description "microbial" encompasses microscopic organisms (microbes, microorganisms) such as bacteria and unicellular eukaryotic organisms. Microbial "growth" is defined as survival or any reproduction of the microbes. A "consortium" is a group of two or more microbial species present in a single culture. A "culture" refers to a single bioreactor containing a growth medium and two or more groups of microbial organisms. A "waste stream" is a medium containing compounds that are generated in a production process, wherein these compounds can not be re-cycled back to the production process or recovered as a useful product.

Environmental samples containing microorganisms for acclimatization may be obtained from sites of production where chlorinated carbohydrates are likely to be present, for example, waste solutions, waste deposits such as sludge and sediments, and soil in the vicinity of a production site. The environmental sample containing microorganisms is enriched and acclimatized for desired performance by culturing in a synthetic medium which mimics the composition and temperature of the waste stream. Generally these conditions include from 0% to 4.5% by weight chloride salt, more typically from 1% to 4.5%, and a temperature between 15° C. and 55° C. The synthetic medium contains a food source for the microorganisms, such as yeast extract (source of nitrogen, amino acids and vitamins) and sugar (carbon source), as well as inorganic salts (for example calcium, sodium, phosphate, sulfate, etc.) and trace elements (such as Fe, Mn, Ni, Mo, Co, Se, etc.) which are important for the growth of microbes. Survival and growth of different microorganisms present in the sample will depend on the initial food source, concentration of chloride salt, and temperature conditions. In one embodiment, the microorganism cultures are incubated at a temperature between about 27° C. to about 50° C. and the medium has a final chloride salt concentration of about 4.5% or less. The salt content may be composed of any chloride salt or combination of chloride salts, including alkali metals, alkaline earth metals, and transition metals, e.g., NaCl, $CaCl_2$, $MgCl_2$, $MnCl_2$, etc., and ammonium chloride. The pH of the medium may be adjusted to optimize conditions for biodegradation of waste streams.

Examples 1 and 2 describe one method of developing and selecting a consortium of microorganisms acclimatized to grow at a specific temperature and salt concentration. In general, an environmental sample containing microorganisms with the potential to degrade chlorinated carbohydrates is cultured in a bioreactor in synthetic medium containing organic components, solvents, and acids usually found in the waste stream that is the source of the chlorinated carbohydrates. For example, in one embodiment, the source of chlorinated carbohydrates is a waste stream from a sucralose production process which also contains one or more of methanol, ethanol, phosphoric acid, dimethylamine HCl (DMA), dimethylformamide (DMF), and dimethylacetamide (DMAc). Temperature and salt concentration of the medium is raised gradually in a stepwise manner. In general, the microorganisms are first acclimatized to a particular temperature and are then acclimatized to a particular salt concentration while maintained at the desired temperature. At each step of temperature or salt increase the culture medium is monitored for degradation of organic components. When the culture is capable of degrading all organic components in the medium at a given temperature or salt concentration, a further increase in temperature or salt is made. This process is repeated until the final desired temperature and salt concentration are reached. The length of the acclimatization process will depend on temperature, salt concentration, and the concentration of microorganisms capable of degrading organic compounds in the medium.

Cultures capable of degrading all organic components in the synthetic medium are then introduced to a medium containing chlorinated carbohydrates, for example, a waste stream, and monitored for the ability to degrade chlorinated carbohydrates, as described in Example 3. The chlorinated carbohydrate-containing medium may be added directly or combined with the synthetic medium and gradually introduced at increasing concentrations. For each culture, the selected temperature and salt conditions are maintained. Each culture capable of degrading one or more chlorinated carbohydrate compounds under specific temperature and salt conditions forms a consortium. Precise identification of the microorganisms present in the consortium is optional. Using the method described in Examples 1-3, eight consortia of microorganisms capable of degrading chlorinated carbohydrates were selected and deposited with the NRRL. Accession numbers and temperature and salt conditions for each consortium are listed in Table 1.

TABLE 1

Characteristics of Consortia Deposited with NRRL

| Consortium # | Accession # | Temp ° C. | Salt % |
|---|---|---|---|
| P-1 | NRRL B-50091 | 27 | 4.5 |
| P-2 | NRRL B-50092 | 30 | 4.5 |
| P-3 | NRRL B-50093 | 37 | 4.5 |
| P-4 | NRRL B-50094 | 45 | 4.5 |
| P-5 | NRRL B-50095 | 45 | 1.0 |
| P-6 | NRRL B-50096 | 45 | 2.0 |
| P-7 | NRRL B-50097 | 45 | 3.0 |
| P-8 | NRRL B-50098 | 50 | 4.5 |

For biodegradation of chlorinated carbohydrates, a medium (e.g., a waste stream) containing these compounds is inoculated with a consortium of microorganisms capable of digesting chlorinated carbohydrates under the temperature and salt conditions found in that medium. The chlorinated carbohydrates may include, but are not limited to, chlorinated mono-, di-, tri-, poly-, or oligosaccharides. The consortium used may be selected for the types of chlorinated carbohydrates it degrades or to optimize biodegradation under a particular temperature or salt condition. Incubation conditions may be selected to optimize degradation of chlorinated carbohydrates in a particular type of medium.

The microbial consortium is acclimatized to degrade one or more chlorinated carbohydrates. Preferably, the microbial consortium degrades sucralose and/or at least one or at least two other chlorinated carbohydrates.

EXAMPLES

1. Selection of Microbial Consortia that Grow at Defined Salt and Temperature Conditions Bucket-style bioreactors were created from 7.5 gallon NALGENE® plastic graduated cylindrical tanks. Air was delivered to the medium via an aquarium air stone. Air flow (L/min) was controlled by a Rotameter. The bioreactor was heated with a Pro-Heat 200 Watt IC titanium aquarium heater, which was digitally controlled by a temperature controller. Medium pH was maintained at 7.0 with $H_2SO_4$ by a Mettler TOLEDO® pH2100e controller, connected to control the acid pump directly. Permeation with medium was achieved with two L-shaped stainless steel tubes mounted on each side of the bioreactor, one for inlet of broth and one for return of biomass. Biomass was separated from permeate via a hollow fiber cartridge containing either an XM-50 or PM-100 membrane, connected to a pump.

Each bioreactor was weighed and weight monitored and maintained by addition of deionized water to compensate for evaporation.

The initial environmental samples were taken from basin sediment from a sucralose production waste-water treatment facility in McIntosh, Ala. The samples were incubated in a synthetic medium consisting of sodium acetate (7.05 g/L), sodium formate (3.16g/L), sucrose (7.6 g/L), yeast extract (0.01 g/L), dimethylamine-HCl (0.272 g/L), dimethylformamide, 99% (0.25 ml/L), dimethylacetamide, 99% (0.125g/L), methanol, 99% (0.165 ml/L), ethanol, 99% (0.04 ml/L), phosphoric acid, 85% (0.165 ml/L), and ammonium hydroxide, 29% (0.225 ml/L). The pH of the medium was adjusted to 7.0 with NaOH. For a 10 L bioreactor, 5 L of this synthetic medium was diluted with 4 L of $H_2O$, and 1 L of environmental sample (basin sediment and basin water) was added to the bioreactor. Initially bioreactors were maintained at a temperature of 27° C.

Degradation of organic salts, solvents, and sucrose in the medium was monitored every 24 h. Microbes were considered acclimatized when all medium components were consumed (degraded) within about 24 h for 3 consecutive days. After this time, the temperature was increased in a step-wise fashion over time from 27° C. to 32° C., to 37° C., to 45° C., to 50° C. At each step, microbes were again "acclimatized" to degrade all medium components at the new temperature within 24 h. This procedure continued until the desired temperature was reached. For temperatures higher than 45° C., it was necessary to introduce the temperature increase even more gradually, allowing 6 weeks or more between temperature increases, to maintain biodegradation.

Figure 1:
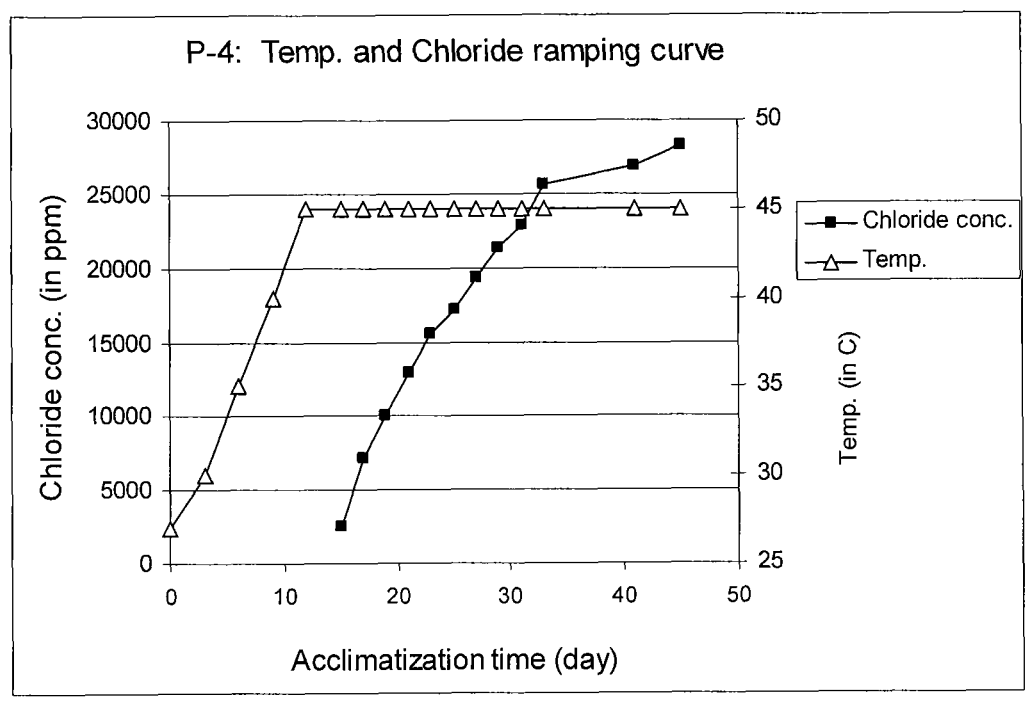
FIG. 1. Salt and temperature ramping curves for acclimatizing consortium P-4 to culture conditions comprising 45° C. and 4.5% salt.

When a consortium was acclimatized to the desired temperature, the concentration of the synthetic medium was increased gradually from 50% to 100% in 10% increments. Salt (chloride) concentration increased with increasing concentration of synthetic medium, with 100% synthetic medium containing approximately 4.5% chloride salt. The chloride level in each batch of medium was measured and adjusted with NaCl to produce medium containing 1, 2, 3, or 4.5% chloride salt. Degradation of organic components in the medium was monitored as described below and the microbes were allowed to acclimatize to each new concentration of chloride salt and synthetic medium. An example of salt and temperature ramping curves for consortium P-4, is shown in FIG. 1.

Full acclimatization of the consortia to final desired temperature and salt concentration required from about one (low temperature or salt) to about six (high temperature and high salt) months.

2. Selection of Microbial Consortia that Degrade Organics in the Medium

Throughout the process described in Example 1, the bioreactor cultures were monitored for degradation of organic components in the medium, in general by liquid or gas chromatography. Bioreactor cultures capable of degrading all organic components in the synthetic medium consistently at the desired temperature and salt concentration for 7-10 days were selected for acclimatization to a sucralose waste stream.

3. Selection of Microbial Consortia that Degrade Chlorinated Carbohydrates

Bioreactors selected by the process described in Example 2 were first exposed to a sucralose waste stream in which the chlorinated carbohydrates had been chemically de-chlorinated, although this step is not essential to the acclimatization procedure. De-chlorination consisted of raising the pH of the waste stream sample to 12 with NaOH, boiling the solution for 1 h, then reducing the pH to 7.5-8.0 with HCl. The solution containing de-chlorinated carbohydrates was gradually introduced into the synthetic medium in increments of 10% and the microbes were allowed to acclimatize to each increase. When the microbes demonstrated the ability to fully degrade all organic components in the medium, the percentage of de-chlorinated carbohydrate medium was increased.

After stabilization for 7-10 days in 100% de-chlorinated carbohydrate solution, the consortia were fed with a raw sucralose waste stream containing chlorinated carbohydrates. The waste stream component was added to achieve approximately 1500 ppm of chlorinated carbohydrates in the de-chlorinated carbohydrate solution. Cultures were fed one of two waste streams that were derived from different steps in the sucralose production process. Chlorinated carbohydrates present in the bioreactor medium before (baseline) and after feeding with the sucralose waste stream (time zero), and at increasing times of incubation of sucralose waste stream with the microbial consortia, were measured by HPLC analysis. The sucralose waste stream component containing chlorinated carbohydrates was added only once to each bioreactor solution. Levels of chlorinated carbohydrates present in the bioreactor solution were measured daily.

Figure 2A:
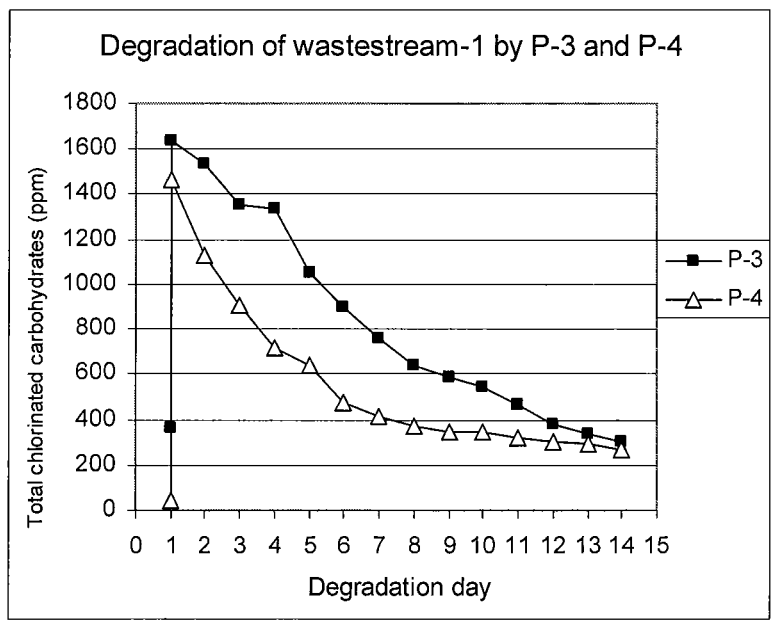
FIG. 2. Biodegradation of total chlorinated carbohydrates in two waste streams produced at different stages of the sucralose production process.
Figure 2B:
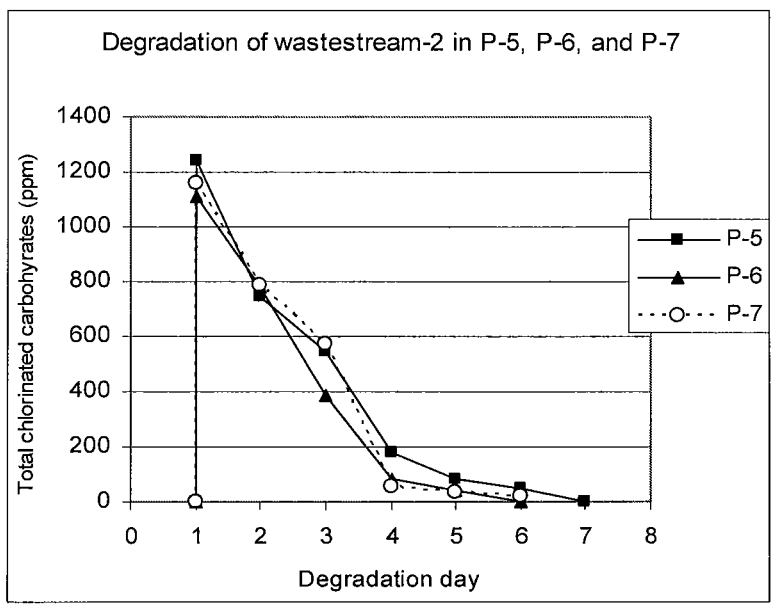

Eight bioreactor cultures demonstrating biodegradation of chlorinated carbohydrates were selected as consortia for deposit with the NRRL. These microbial consortia can be maintained in a waste stream medium, or can be stored in residual medium containing 15% glycerol at −80° C. Temperature and chloride salt parameters for these eight consortia are shown in Table 1. FIG. 2 demonstrates the progression of the biodegradation of total chlorinated carbohydrates in the two waste streams by consortia P-3 and P-4 (FIG. 2A) and consortia P-5, P-6, and P-7 (FIG. 2B).

4. Use of Consortia to Degrade Chlorinated Carbohydrates in a Sucralose Production Waste Stream The compositions of chlorinated carbohydrates in consortium cultures prior to (baseline) and at increasing times after exposure to the waste streams are shown in Tables 2 and 3. For consortia P3 and P4, approximately 82% of the chlorinated carbohydrates in waste stream 1 and approximately 47-53% of the chlorinated carbohydrates in waste stream 2 were degraded over seven days.

Di-chlorinated disaccharides in Tables 2 and 3 include, but are not limited to, 4,1'-dichlorogalactosucrose; 4,1'-dichloro-3 ',6'-anhydrogalactosucrose, 4,6'-dichlorogalactosucrose; 1',6'-dichlorosucrose; and 6,6'-dichlorosucrose. Trichlorinated disaccharides include, but are not limited to, 4,1',6'-trichlorosucrose; 4,1',6'-trichlorogalactosucrose; 4,6,6'-trichlorogalactosucrose; and 6,1',6'-trichlorosucrose. Tetrachlorinated disaccharides include, but are not limited to, 4,1',4',6'-tetrachloro-galacto-tagato-sucros and 4,6,1',6'-tetrachlorogalactosucrose. Penta-chlorinated carbohydrates are also believed to be degraded. The second waste stream contained additional compounds that were also degraded by the consortia. These compounds have not yet been identified and may include additional chlorinated carbohydrates (data not shown).

As shown in FIG. 3, the microbial consortia also degraded 4-chlorogalactose that was added to synthetic medium, demonstrating that they are also capable of degrading monochlorinated monosaccharides.

TABLE 2

Biodegradation of chlorinated carbohydrates in waste stream 1. Values represent total quantities (ppm) of each class of chlorinated carbohydrate.

| Sample Name | Di-chlorinated carbohydrates | Tri-chlorinated carbohydrates | Tetra-chlorinated carbohydrates | Total |
|---|---|---|---|---|
| P-3 Baseline | 20 | 340 | 0 | 361 |
| P-3 Time 0 | 918 | 446 | 270 | 1634 |
| P-3 Day 1 | 832 | 434 | 264 | 1530 |
| P-3 Day 2 | 702 | 397 | 257 | 1356 |
| P-3 Day 3 | 686 | 380 | 272 | 1337 |
| P-3 Day 4 | 536 | 279 | 232 | 1048 |
| P-3 Day 5 | 468 | 235 | 191 | 894 |
| P-3 Day 6 | 401 | 160 | 195 | 757 |
| P-3 Day 7 | 89 | 29 | 181 | 299 |
| P-4 Baseline | 39 | 0 | 0 | 39 |
| P-4 Time 0 | 977 | 194 | 294 | 1466 |
| P-4 Day 1 | 693 | 143 | 295 | 1131 |
| P-4 Day 2 | 497 | 118 | 288 | 903 |
| P-4 Day 3 | 365 | 79 | 274 | 718 |
| P-4 Day 4 | 294 | 59 | 281 | 634 |
| P-4 Day 5 | 204 | 41 | 230 | 475 |
| P-4 Day 6 | 151 | 33 | 233 | 417 |
| P-4 Day 7 | 43 | 36 | 191 | 270 |

TABLE 3

Biodegradation of chlorinated carbohydrates in waste stream 2. Values represent total quantities in ppm of each class of chlorinated carbohydrate.

| Sample Name | Di-chlorinated carbohydrates | Tri-chlorinated carbohydrates | Tetra-chlorinated carbohydrates | Total |
|---|---|---|---|---|
| P-3 Baseline | 9 | 0 | 119 | 128 |
| P-3 Time 0 | 133 | 1020 | 100 | 1254 |
| P-3 Day 1 | 109 | 1020 | 100 | 1230 |
| P-3 Day 2 | 96 | 921 | 91 | 1108 |
| P-3 Day 3 | 65 | 809 | 88 | 963 |
| P-3 Day 4 | 53 | 721 | 89 | 862 |
| P-3 Day 5 | 41 | 658 | 83 | 781 |
| P-3 Day 6 | 26 | 551 | 87 | 664 |
| P-4 Baseline | 31 | 0 | 116 | 147 |
| P-4 Time 0 | 154 | 1127 | 102 | 1383 |
| P-4 Day 1 | 114 | 1096 | 81 | 1291 |
| P-4 Day 2 | 82 | 955 | 89 | 1125 |
| P-4 Day 3 | 35 | 888 | 81 | 1004 |
| P-4 Day 4 | 18 | 768 | 79 | 865 |
| P-4 Day 5 | 14 | 658 | 64 | 736 |
| P-4 Day 6 | 5 | 566 | 74 | 645 |

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. An isolated microbial consortium capable of degrading one or more chlorinated carbohydrates selected from the group consisting of 4,1',4',6'-tetrachloro-galacto-tagato-sucrose, 4,6,1',6'-tetrachlorogalactosucrose, 4,1',6'-trichlorosucrose and 4,6'-dichlorosucrose, and wherein the isolated microbial consortium can grow or survive in a medium comprising said one or more chlorinated carbohydrates.

2. The isolated microbial consortium of claim 1, wherein the medium comprises a waste stream generated in a sucralose production process.

3. The isolated microbial consortium of claim 1, comprising at least one of the deposited bacterial species selected from the group consisting of NRRL B-50091, NRRL B-50092, NRRL B-50093, NRRL B-50094, NRRL B-50095, NRRL B-50096, NRRL B-50097, and NRRL B-50098.

4. The isolated microbial consortium of claim 1, wherein the medium comprises about 4.5 percent or less chloride salt.

5. The isolated microbial consortium of claim 4, wherein the medium comprises chloride salt in the range of from about 1 percent to about 4.5 percent.

6. The isolated microbial consortium of claim 1, wherein the microbial consortium is capable of growing or surviving in the medium at a temperature in the range of from about 15° C. to about 55° C.

7. The isolated microbial consortium of claim 6, wherein the microbial consortium is capable of growing or surviving in the medium at a temperature in the range of from about 27° C. to about 50° C.

8. The isolated microbial consortium of claim 1, wherein the microbial consortium is capable of degrading 4,1',4',6'-tetrachloro-galacto-tagato-sucrose.

9. The isolated microbial consortium of claim 8, wherein the microbial consortium is also capable of degrading sucralose.

10. The isolated microbial consortium of claim 1, wherein the microbial consortium is capable of degrading 4,1',6'-trichlorosucrose.

11. A method for degrading chlorinated carbohydrates, the method comprising the steps of a) inoculating a medium containing the chlorinated carbohydrates with the isolated microbial consortium of claim 1; and b) incubating the isolated microbial consortium in the medium.

12. A method for degrading one or more chlorinated carbohydrates selected from the group consisting of 4,1',4',6'-tetrachloro-galacto-tagato-sucrose, 4,6,1',6'-tetrachlorogalactosucrose, 4,1',6'-trichlorosucrose and 4,6'-dichlorosucrose, the method comprising the steps of a) inoculating a medium containing the one or more chlorinated carbohydrates with an isolated microbial consortium capable of degrading at least one of 4,1',4',6'-tetrachloro-galacto-tagato-sucrose, 4,6,1',6'-tetrachlorogalactosucrose, 4,1',6'-trichlorosucrose and 4,6'-dichlorosucrose; and b) incubating the microbial consortium in the medium.

13. The method of claim 12, wherein the medium comprises a waste stream generated in a sucralose production process.

14. The method of claim 12, wherein the chlorinated carbohydrates are generated in a sucralose production process.

15. The method of claim 12, wherein the microbial consortium is also capable of degrading sucralose.

16. The method of claim 12, wherein the microbial consortium is capable of degrading 4,1',4',6'-tetrachloro-galacto-tagato-sucrose.

17. The method of claim 12, wherein the medium comprises chloride salt at a concentration of about 4.5 percent or less.

18. The method of claim 17, wherein the medium comprises chloride salt in the range of from about 1 percent to about 4.5 percent.

19. The method of claim 12, wherein the incubation temperature of the medium is in the range of from about 15° C. to about 55° C.

20. The method of claim 19, wherein the incubation temperature of the medium is in the range of from about 27° C. to about 50° C.

21. The method of claim 12, wherein the microbial consortium is capable of degrading 4,1',6'-trichlorosucrose.

22. A method for developing a microbial consortium capable of degrading one or more chlorinated carbohydrates selected from the group consisting of 4,1',4',6'-tetrachlorogalacto-tagato-sucrose, 4,6,1',6'-tetrachlorogalactosucrose, 4,1',6'-trichlorosucrose and 4,6'-dichlorosucrose, comprising the steps of a) providing an environmental sample containing microbes; b) incubating microbes in the sample in a defined medium comprising one or more organic solvents, wherein the temperature of incubation is from about 15° C. to about 55° C. and the chloride salt concentration of the medium is about 4.5 percent or less; c) selecting a microbial consortium present in the medium after step b) that degrades one or more of the organic solvents; d) subsequently replacing the medium of the selected consortium with a medium comprising the one or more chlorinated carbohydrates, and e) selecting a consortium that degrades the one or more chlorinated carbohydrates.

23. A method of producing sucralose comprising the steps of a) maintaining a solution comprising a sucralose-6-acylate in an aqueous solvent under conditions sufficient to deacylate substantially all of the sucralose-6-acylate; b) subsequently recovering the sucralose; and c) degrading one or more chlorinated carbohydrates selected from the group consisting of 4,1',4',6'-tetrachloro-galacto-tagato-sucrose, 4,6,1',6'-tetrachlorogalactosucrose, 4,1',6'-trichlorosucrose and 4,6'-dichlorosucrose present after the deacylation by a method comprising the steps of i) inoculating a solution comprising the one or more chlorinated carbohydrates with the isolated microbial consortium of claim 1 and ii) incubating the microbial consortium in the solution.

24. An isolated microbial consortium capable of degrading 4,1',4',6'-tetrachloro-galacto-tagato-sucrose.

\* \* \* \* \*